US005580569A

United States Patent [19]

Giampapa

[11] Patent Number: 5,580,569
[45] Date of Patent: *Dec. 3, 1996

[54] ARTICLE FOR TISSUE-SPECIFIC DELIVERY OF THERAPEUTIC AGENTS

[76] Inventor: Vincent C. Giampapa, 46 Highland Ave., Montclair, N.J. 07042

[ * ] Notice: The portion of the term of this patent subsequent to Jun. 28, 2013, has been disclaimed.

[21] Appl. No.: 145,569

[22] Filed: Nov. 4, 1993

Related U.S. Application Data

[63] Continuation-in-part of Ser. No. 876,783, Apr. 30, 1992, Pat. No. 5,326,568, and Ser. No. 82,419, Jun. 28, 1993, Pat. No. 5,494,677.
[51] Int. Cl.$^6$ ................ A61F 2/02; A61K 9/24; A61M 31/00; A61B 17/36
[52] U.S. Cl. .......... 424/426; 514/772.6; 514/774; 514/953; 604/57; 606/46
[58] Field of Search ................. 424/423, 426; 514/953, 772.6, 774; 604/57; 606/46

[56] References Cited

U.S. PATENT DOCUMENTS

| 4,771,757 | 9/1988 | Chevalier | 124/51 R |
| 4,863,428 | 9/1989 | Chevalier | 604/130 |

*Primary Examiner*—Carlos Azpuru
*Attorney, Agent, or Firm*—M. K. Silverman

[57] ABSTRACT

An article for tissue-specific delivery of therapeutic agents constitutes a substrate of a material that is biodegradable in situ in human tissue, which substrate is configured into a projectile and proportioned for insertion into a channel of an endoscope, the substrate having incorporated thereinto selectable therapeutic agents to be delivered, the projectile including, upon an exterior surface, a capacity for tissue affixation to the tissue of interest.

8 Claims, 5 Drawing Sheets

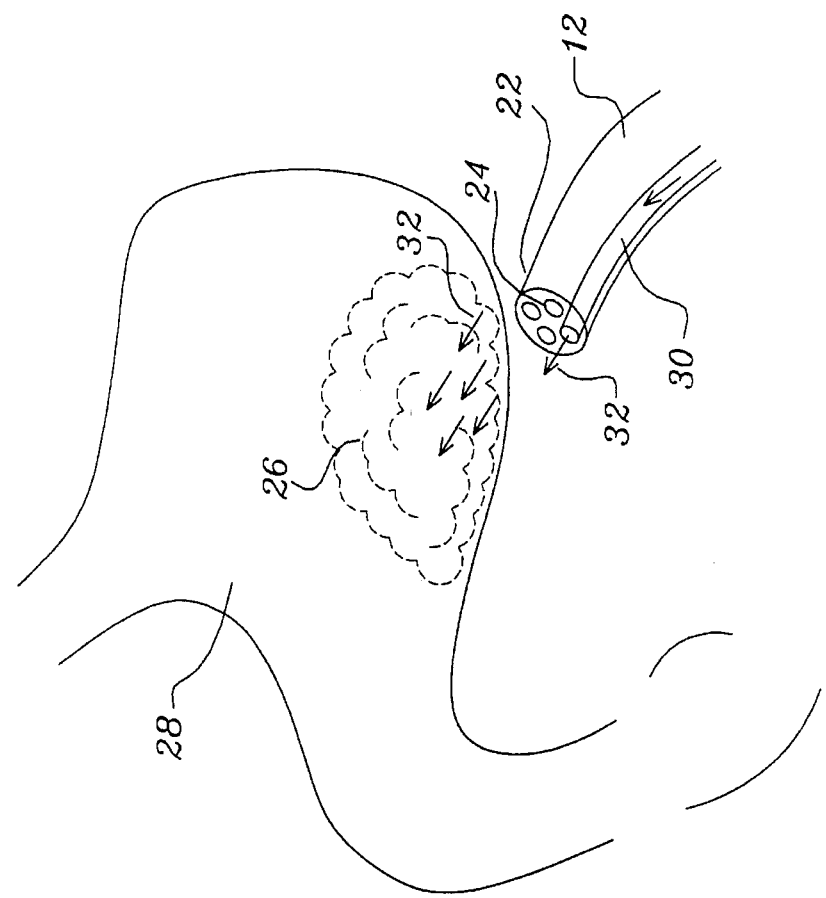
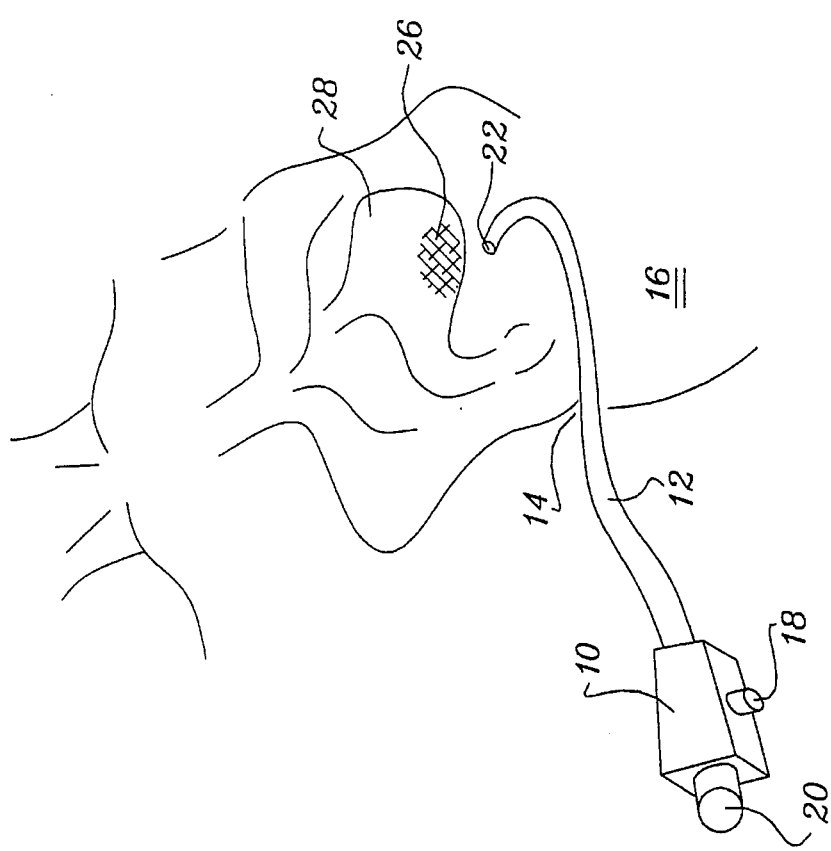

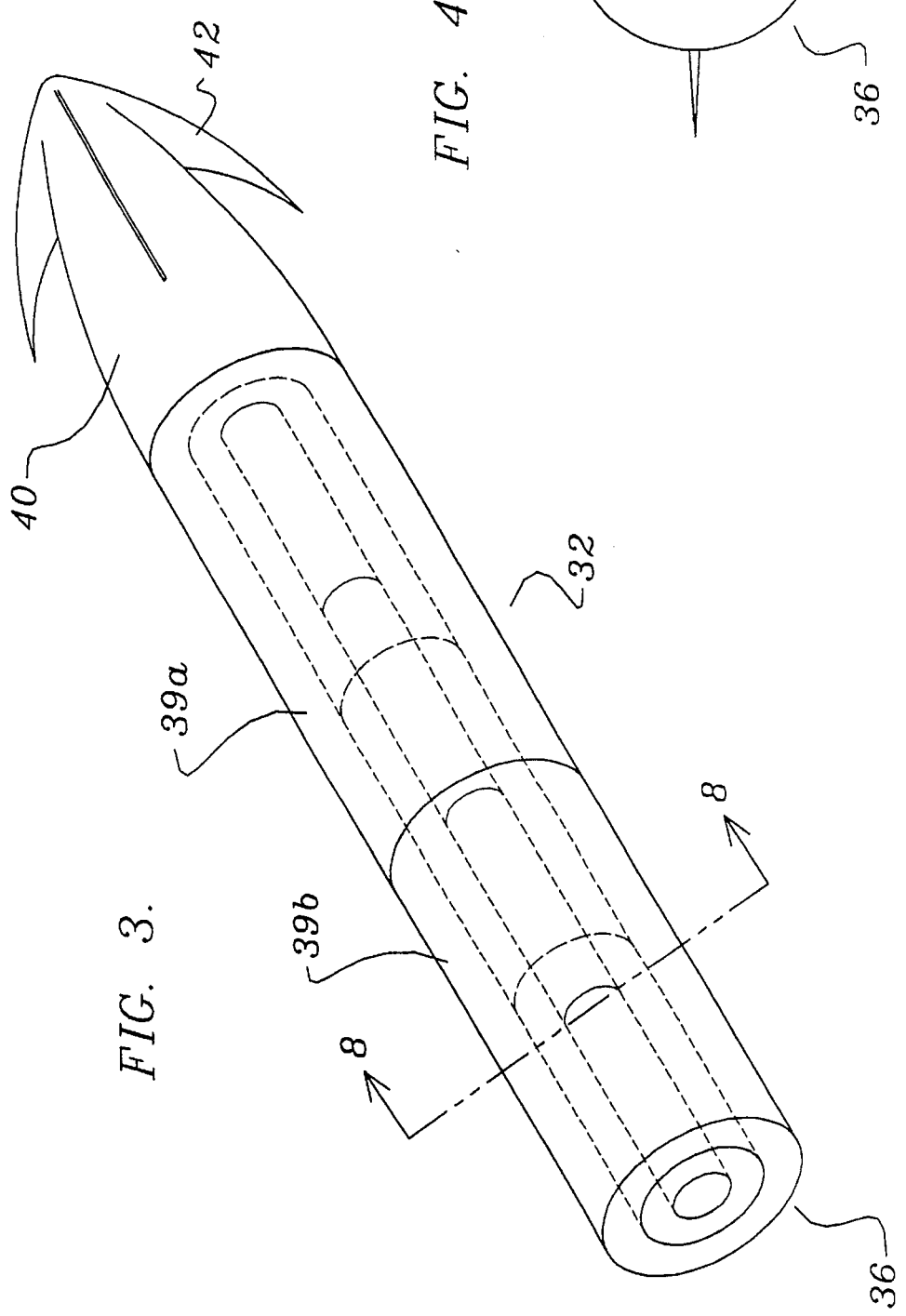

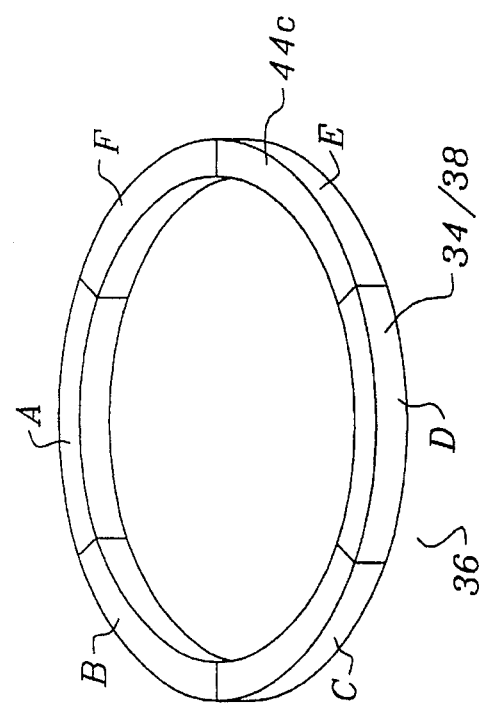
FIG. 8.
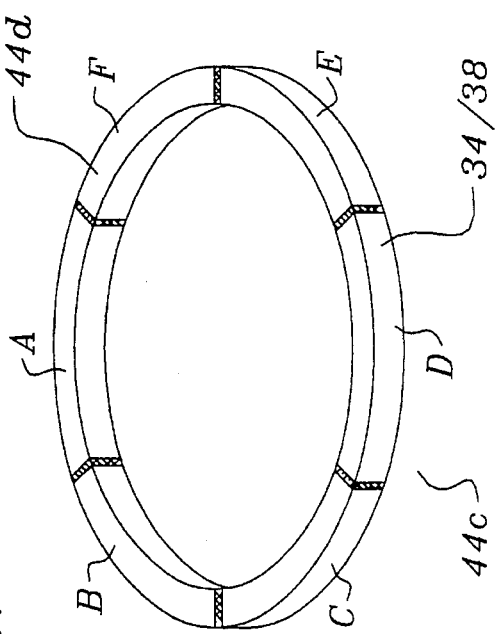
FIG. 9.
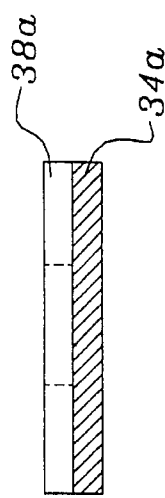
FIG. 5A.
FIG. 5B.
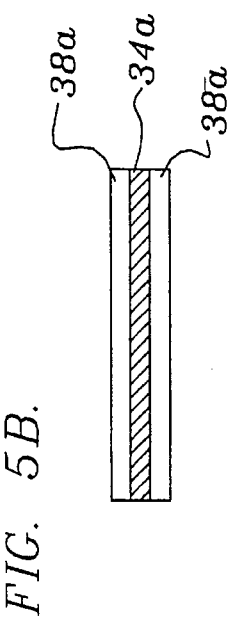
FIG. 6.
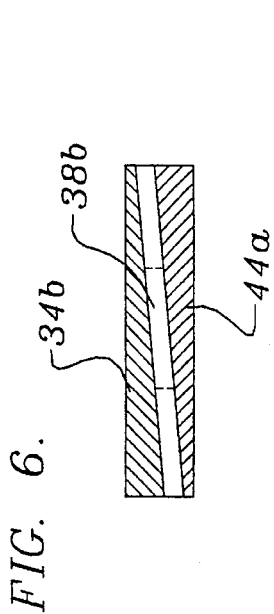
FIG. 7.
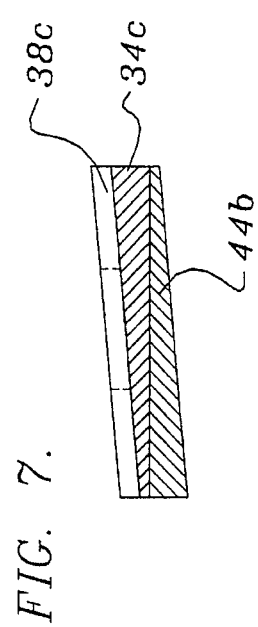

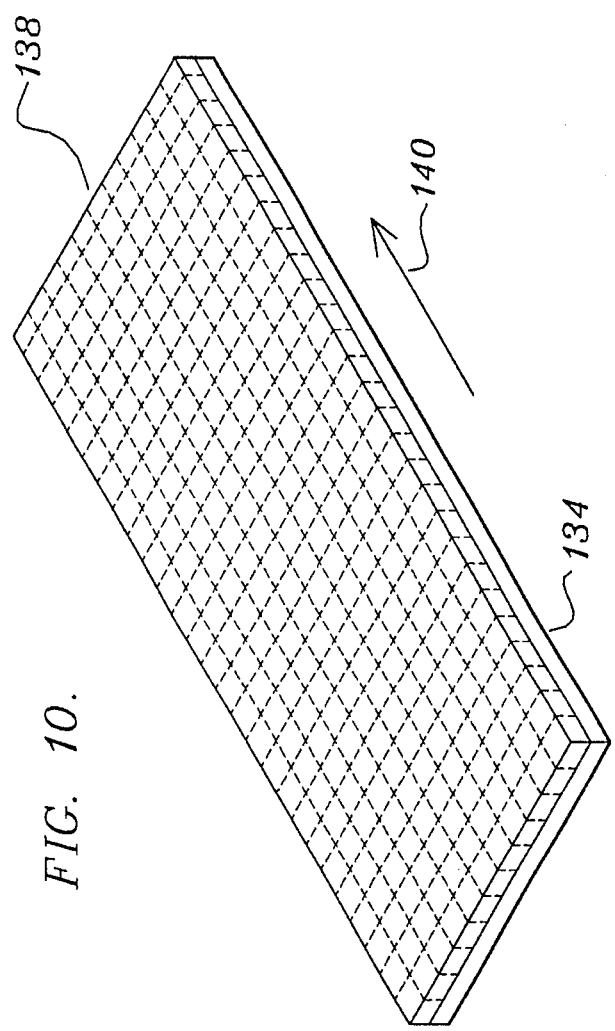
FIG. 10.
FIG. 11.
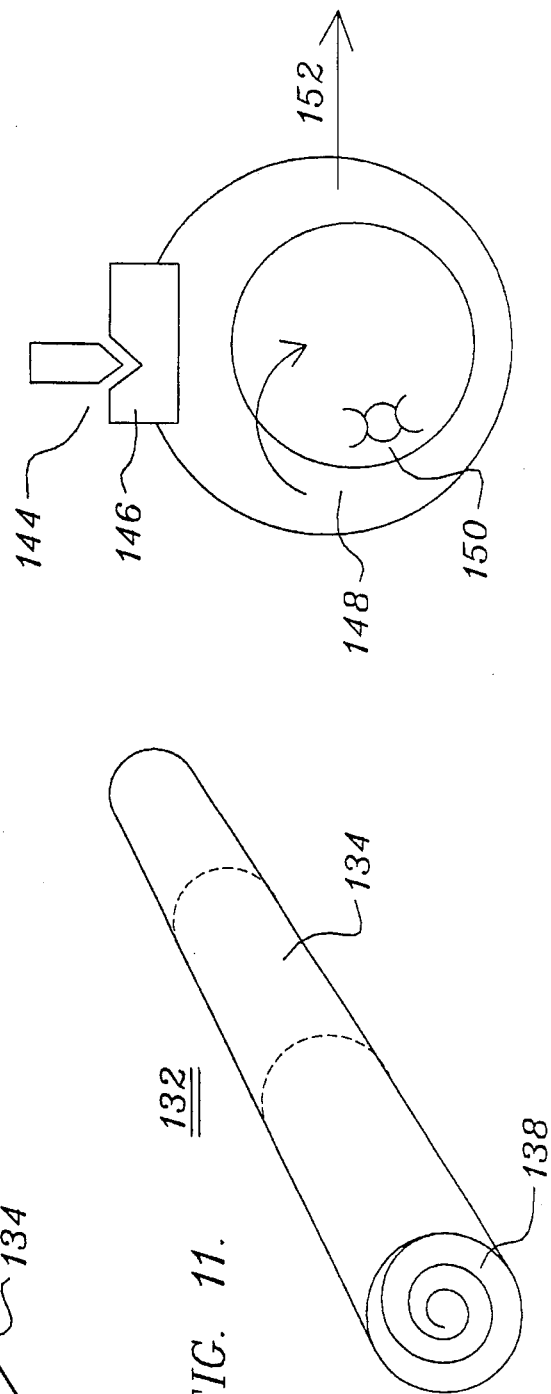
FIG. 12.

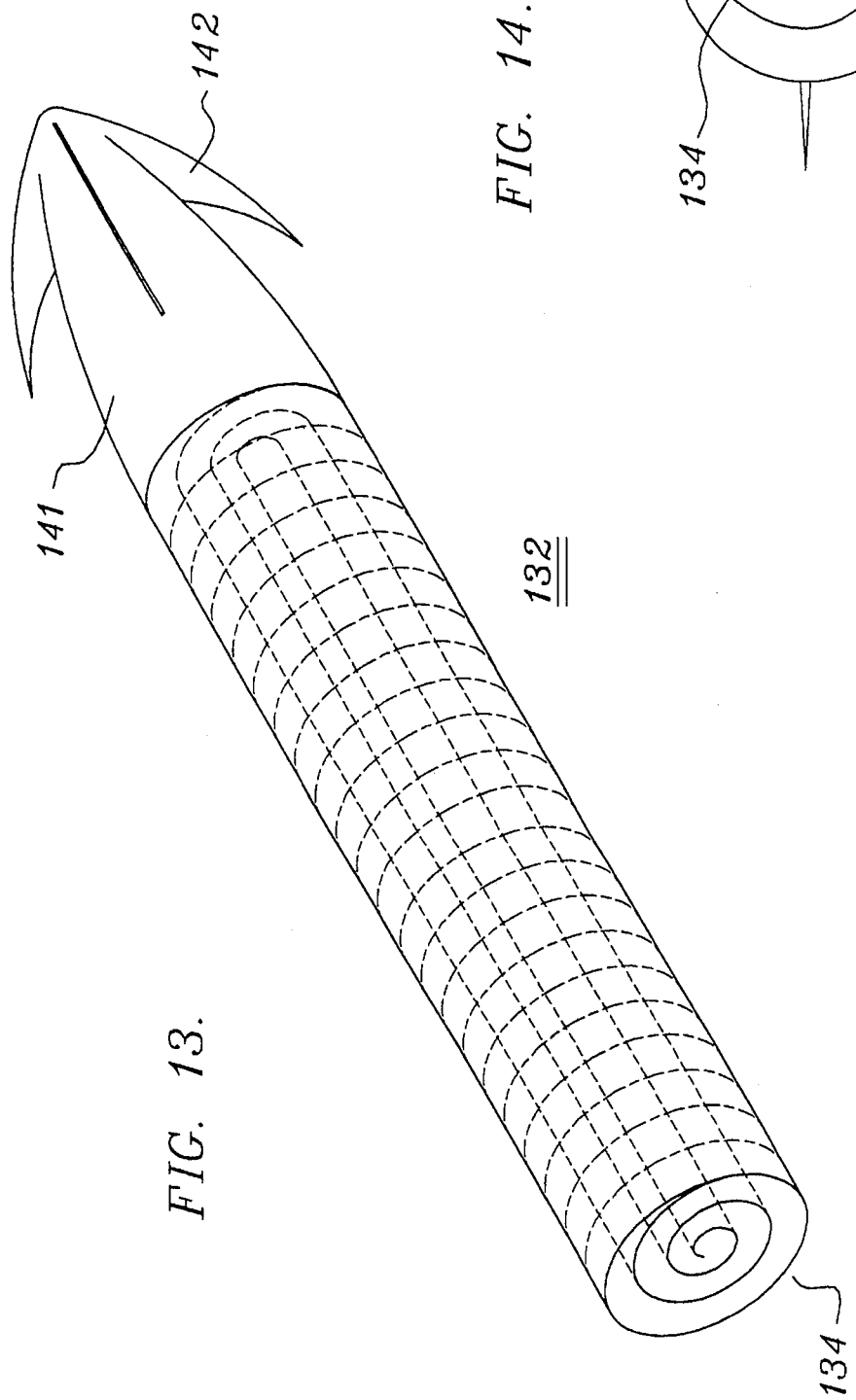

ARTICLE FOR TISSUE-SPECIFIC DELIVERY OF THERAPEUTIC AGENTS

REFERENCE TO RELATED APPLICATION

This case is a continuation in part of applications Ser. No. 07/876,783, filed Apr. 30, 1992, now U.S. Pat. No. 5,326,568, and Ser. No. 08/082,419, filed Jun. 28, 1993, now U.S. Pat. No. 5,494,677.

BACKGROUND OF THE INVENTION

Biodegradable materials have been known in the art for a number of years. More particularly, in the literature of medical research relative to such materials, reference is made to the following biodegradable materials:

Processed sheep dermal collagen (PSDC), Hench's bioglass, surgical grade polyurethanes, fibrinogens, polyiminocarbonates, poly (L-lactic) acid (also known as polylactic acid), and polyglycolic acid, Representative articles in the literature relative to the above are: "Structure and Property Relationships for Design of Polyiminocarbonates," by Pulapura, et al, *Biomaterials*, 1990 (119): 666–78, "Rate Controlled Drug Delivery Systems: Controlled Release versus Sustained Released" by Chien in *Medical Progress Technology* 1989, 15 (1–2): 11–14; and "Enzymatic Activity Toward Poly (L-Lactic) Acid Implants by Schakenraad, et al, *Jour. Biomedical Materials Research*, 1990 May, 24(5):529–45.

The earliest known reference to a biodegradable tissue implant is West German Patent No. 2,424,169 (1974) to Little.

Much publicity has attended the so-called Norplant elements employed as birth control means and, as such, the Norplant has become well known among contemporary biodegradable materials.

Accordingly, medical research has now established, beyond question, the value of subcutaneous, and other implantation of therapeutic and pharmacologic agents within a biodegradable carrier to facilitate the potentiation or concentration of the agent within cellular tissue at a location which will maximize its benefit to the patient. The present invention is accordingly concerned with an improvement in the form and structure of the biodegradable drug carrier to effect a physical attachment at an internal site Thereby, enhanced delivery of a necessary drug or nutrient can be accomplished at a tissue specific internal site, thereby reducing the need for systemic treatment.

The instant invention is an improvement of my above referenced inventions, which provides for a configuration of the biodegradable substrate into the form of a projectile for tissue-specific delivery by an endoscope, such as a laparoscope, bronchoscope and laryngoscope.

SUMMARY OF THE INVENTION

The present invention relates to an article for tissue-specific delivery of therapeutic agents. The article, more particularly, comprises a substrate of a material that is biodegradable in situ in human tissue, said substrate configured into a projectile and proportioned for insertion into a channel of an endoscope, said substrate having incorporated thereinto selectable therapeutic agents to be delivered, said projectile including, upon an exterior surface thereof, means for tissue affixation.

It is an object of the present invention to provide an implantable biodegradable pharmakinetic agent release system.

It is another object of the invention to provide an in vivo biodegradable implant for delivery of different bioactive agents over respectively differing time intervals, at a specific physiological site.

It is a further object to provide an internally implantable biodegradable implant.

The above and yet other objects and advantages of the present invention will become apparent from the hereinafter set forth Brief Description of the Drawings, Detailed Description of the Invention, and claims appended herewith.

BRIEF DESCRIPTION OF THE DRAWINGS

FIG. 1 is a conceptual view showing insertion of an endoscope through the abdominal wall, the head thereof reaching a tumor site in the abdominal cavity, in the course of a laparoscopic examination.

FIG. 2 is an enlarged view of the end of said endoscope and of a tumor into which biodegradable projectiles in accordance with the instant invention are delivered.

FIG. 3 is a perspective view of the inventive article.

FIG. 4 is a rear plan view of FIG. 3.

FIGS. 5A to 7 are conceptual enlarged views of segments of the substrate of the biodegradable projectile.

FIG. 8 is a conceptual view of a radial cross-section of the article of FIG. 3.

FIG. 9 is a view, similar to the view of FIG. 8, however showing a variation thereof.

FIG. 10 is a view of a substrate used in a second embodiment of the invention.

FIG. 11 is a view of the substrate of FIG. 10 when rolled into a spiral configuration.

FIG. 12 is a conceptual diagram of the cellular action of the invention.

FIG. 13 is a view, similar to the view showing the spiral configuration of the substrate, but inclusive of the barb structure thereof.

FIG. 14 is a rear plan view of FIG. 13.

DETAILED DESCRIPTION OF THE INVENTION

With reference to the view of FIG. 1 there is schematically shown the operation of one type of endoscope, that is, a laparoscope 10. As is well known in the art, the laparoscope is, in contemporary surgery, employed in a broad range of surgical procedures generally termed laparoscopies. In such procedures, an elongated flexible longitudinal member 12 enters the patient's body through an incision 14 and, once inside body cavity 16, is positioned through the use of laparoscope controls 18 in association with video monitor 20. More particularly, as may be seen in the view of FIG. 2, head 22 of the laparoscope is provided with one or more micro video cameras 24 to enable the surgeon to observe the environment about the head 22 within body cavity 16.

A typical prior art laparoscope, head 22 is advanced to the site of a tumor 26, shown in the examples of FIGS. 1 and 2 to be tumor 26 within stomach 28. In such prior art use of a laparoscope, when the head 22 of flexible member 12 has reached the site of tumor 26, the tumor is observed and photographed. Then a laser may be employed to excise the tumor from the tissue to which it has become attached.

Further, many state-of-the-art laparoscopes are provided with a channel 30 through which liquid medication may be selectably applied to the tumor site by the physician through the use of controls 18.

The instant invention builds upon this state-of-the-art use of laparoscopes by providing an article 32 proportioned for delivery through said channel 30 and adapted for delivery to a tumor or surgical site through essentially the same mechanical means by which liquid medication is presently delivered through the laparoscope.

The invention more particularly consists of a reconfiguration of the biodegradable therapeutic agent delivery means set forth in my pending applications Ser. No. 07/876,783, filed Apr. 30, 1992, now U.S. Pat. No. 5,326,568 and Ser. No. 08/082,419, filed Jun. 28, 1993. That is, inventive article 32 (see FIG. 3) is formed of a substrate 34a (see FIG. 5A). of a material that is biodegradable in situ in human tissue. Materials of this type have become well known in the art and are set forth above in the Background of the Invention, however, polylactic and polyglycolic acid comprise the preferred materials for the substrate 34a.

As may be seen in the views of FIGS. 3 and 4 the substrate will, in a preferred embodiment, take the form of a plurality of concentric tubules 36. Such tubules are presently manufactured and available from Biosciences Ltd., of Tampere, Finland.

Incorporated into said substrate 34a are selectable therapeutic agents 38a to be delivered to the surgery or other site in need of potentiated pharmacologic action. As may be noted in the view of FIG. 5A, the therapeutic agent 38a may be adhered upon substrate 34a. However, it is to be appreciated that layers 34a and 38a may be totally integrated into each other. Alternatively layers of the therapeutic agent 38a may be provided above and below substrate 34a. See FIG. 5B.

In FIG. 6 is shown an embodiment in which the release characteristic of therapeutic agent 38b can be controlled by varying the thickness of substrate 34b. With further reference to FIG. 6 it is to be appreciated that, within the structure of substrate 34b may be provided a vaso-inductive or vaso-inhibiting agent 44a such as an angiogenic growth factor or tumor necrosis factor, the respective functions of which are to enhance or diminish the degree of capillary ingrowth of the substrate 34b at the tumor 26 to, in the latter case, decrease tumor size. Any number of physical geometries of relative arrangement of the substrate, the therapeutic agent, and the growth factors may be generated, as may be appreciated from the view of FIG. 7 where there is shown a substrate 34c, therapeutic agent 34c and vaso-inductive agent 44b.

As may be appreciated from the view of FIG. 3 the therapeutic agent provided at different longitudinal segments 39a and 39b of the article 32 within the human tissue can also be selected.

The instant inventive article differs from that set forth in my above referenced co-pending applications in its use of a means for tissue affixation in the nature of anchor 40. See FIGS. 3 and 4. It is to be appreciated that the means for tissue fixation may take many forms including configurations barbs 42 either with or without anchor 40 and, in lieu barb 42, articles 32 having only chemical adhesion means by which to accomplish the affixation of the article to the therapeutic site of interest. There are known in the art many such tissue adhesion-composition including without limitation, fibrin glue or other biologically compatible adhesives.

Where physical means of affixation are employed, the biodegradable material thereof must possess a slower rate of degradation than the substrate.

With reference to the views of FIGS. 8 and 9 there are radii cross-sectional view of the article of FIG. 3. Therefrom, it may be appreciated that further differentiation and combination of therapeutics agents in the instant system may be provided in accordance with the particular angular position on a radial cross-section of a surface of a given tubule 36 while a vaso-inductive or vaso-inhibiting agent 44c is applied to the surface thereof. Accordingly, in the view of FIG. 8 there are shown six different therapeutic agents 38 (at positions A to F) that may be placed longitudinally upon each tubule 36 of the inventive article 32.

In the view of FIG. 9 is shown a variant of the embodiment of FIG. 8 in which a vaso-inductive agent 42d is additionally provided between each substrate segment and therapeutic agent 38 associated therewith. As may be appreciated between the views of FIGS. 5 thru 9, an almost infinite number of interrelationships between substrate, therapeutic agent and vaso-inductive or inhibiting agent may be accomplished within the scope of the present invention.

In the view of FIG. 10 is shown a planar substrate 134 upon which is disposed a matrix 138 of pharmacologic agents. Substrate 134 is then rolled about axis 140 to produce the spiral structure 132 shown in FIG. 11. The result thereof is a system having alternating layers of the biodegradable substrate 134 and the matrix 138, with the substrate forming the outermost layer of the structure 132.

Upon this outermost layer of the rolled substrate is applied a vascular growth factor 144 (see FIG. 12). Growth factors are signal proteins that control tissue regeneration and wound healing. When they are released from the blood or local tissue, such growth factors bind to the high affinity surface membrane receptors 146 of specific target cells 148, triggering proliferation of these target cells via DNA synthesis 150.

The present system utilizes fibroblast growth factor (FGF), one of the most potent of angiogenic growth factors. In microgram quantities, FGF will induce endothelial cells to produce blood vessels. One result thereof is the development of an osmotic pump action 152, shown in FIG. 12.

The above structure is employed in a second embodiment of the invention shown in FIGS. 13 and 14. Therein, in lieu of tubules 36, said substrate 134 is rolled, in "jelly roll" fashion, to form the inventive structure 132. As in the first embodiment, the structure is provided with an anchor 141 and barbs 142.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described my invention what I claim as new, useful and non-obvious and, accordingly, secure by Letters Patent of the United States is:

1. An article for tissue-specific delivery of therapeutic agents, comprising:

a substrate of a material which is bioerodable in situ in human tissue, said substrate configured as a projectile and proportioned for insertion into a channel of an endoscopic instrument, said substrate comprising a matrix including therapeutic agents to be selectably delivered as a function of the bioerosion of said substrate, said projectile including, upon an exterior surface thereof, an angiogenic agent and means for tissue affixation.

2. The article as recited in claim 1, in which said tissue affixation means comprises:

tissue anchoring means.

3. The article as recited in claim 1, in which said tissue affixation means comprises:

tissue adhesion means.

4. The article as recited in claim 2, in which said tissue anchoring means comprises:

a material comprising means for bioerosion at a slower rate than said substrate of said article.

5. The article as recited in claim 1, wherein said substrate includes an agent or growth factor selected from the agents consisting of:

a vaso-inductive agent, a vaso-inhibiting agent, and tumor necrosis factors.

6. The article as recited in claim 5, in which said vaso-inductive agent is selected from the group consisting of: vascular endothelial growth factor, platelet growth factor, vascular permeability growth factor, fibroblast growth factor, and transforming growth factor beta.

7. The article as recited in claim 1, in which said therapeutic agents to be delivered are selected from the group consisting of chemotherapeutics, tumorcidals, analgesics, hormones, enzymes, anesthetics, anti-inflammatories, antibiotics, immunoglobulins, gene therapeutics, and cellular replacement therapeutics and.

8. The article as recited in claim 1 in which the material of said substrate is selected from the group of materials consisting of processed sheep dermal collagen, Hench's bioglass, fibrinogen, polyimino-carbonates, polyglycolic acid and polylactic acid.

* * * * *